United States Patent [19]

Gross

[11] 4,022,878

[45] May 10, 1977

[54] METHODS AND COMPOUNDS FOR PRODUCING SPECIFIC ANTIBODIES

[75] Inventor: Stanley J. Gross, Encino, Calif.

[73] Assignee: Biological Developments, Inc., Encino, Calif.

[22] Filed: Nov. 29, 1974

[21] Appl. No.: 528,044

Related U.S. Application Data

[60] Division of Ser. No. 253,632, May 15, 1972, abandoned, which is a continuation-in-part of Ser. Nos. 45,558, June 11, 1970, abandoned, and Ser. No. 89,929, Nov. 16, 1970, abandoned.

[52] U.S. Cl. .................... 424/1.5; 424/12; 424/88
[51] Int. Cl.$^2$ ................ G01N 33/00; A61R 39/00; G01N 33/16
[58] Field of Search ............ 260/112 R; 424/1, 12, 424/201, 226, 265, 359, 88

[56] References Cited

UNITED STATES PATENTS

| | | | |
|---|---|---|---|
| 3,709,868 | 1/1973 | Spector | 424/12 X |
| 3,766,162 | 10/1973 | Spector | 424/12 X |
| 3,809,782 | 5/1974 | Spector | 424/12 X |
| 3,843,696 | 10/1974 | Wagner et al. | 260/570.8 R X |
| 3,867,366 | 2/1975 | Rubenstein et al. | 424/12 X |
| 3,878,187 | 4/1975 | Schneider et al. | 424/12 X |
| 3,884,898 | 5/1975 | Schneider | 424/12 X |
| 3,888,866 | 6/1975 | Leute et al. | 424/12 X |
| 3,901,654 | 8/1975 | Gross | 424/1 X |

Primary Examiner—Benjamin R. Padgett
Assistant Examiner—Christine M. Nucker
Attorney, Agent, or Firm—McAulay, Fields, Fisher & Goldstein

[57] ABSTRACT

This invention relates to a novel method of producing purified antibodies which are truly specific for native homologous hapten or antigen by administering artificial antigens as described therein to an antibody producing host followed by isolation and purification.

8 Claims, No Drawings

METHODS AND COMPOUNDS FOR PRODUCING SPECIFIC ANTIBODIES

RELATION TO CO-PENDING APPLICATION

This application is a division of co-pending application Ser. No. 253,632, filed May 15, 1972 by Stanley J. Gross, for "METHODS AND COMPOUNDS FOR PRODUCING SPECIFIC ANTIBODIES", abandoned; which is a continuation-in-part of application Ser. No. 45,558, filed June 11, 1970, abandoned; and application Ser. No. 89,929, filed Nov. 16, 1970, abandoned.

BACKGROUND OF THE INVENTION

1. Field of the Invention

This invention relates to a method for the preparation of purified antibodies which are specific for native homologous hapten or antigen. The invention also relates to novel artificial antigens useful for generating such specific antibodies. The antibodies produced in accordance with this invention are useful in immune assay of a wide variety of chemical substances and in particular those of pharmacologic and/or social significance such as the steroids, catechol amines, prostaglandins and drugs of abuse.

This application is a continuation in part of my prior, copending applications Ser. Nos. 45,558, filed June 11, 1970, and 89,929, filed Nov. 16, 1970. The immunologic terms employed herein are believed to be in accord with conventional usage and definition. Should any presently unforseen confusion arise, unless otherwise indicated, the construction of a term shall be in accordance with its definition and usage in the well-known textbook by Weiser, Myrvid and Pearsall, *Fundamentals of Immunology for Students of Medicine and Related Sciences*, published by Lea & Febiger, Philadelphia, 1969.

2. Description of the Prior Art

A relatively new approach to biological assaying involves immunochemical procedures as a basis for the assay. Such procedures involve the use of antibodies which react with the compound to be assayed. A known amount of antibody and the sample, obtained from the test species, are intermixed. Theoretically, if the antibody is specific for the compound to be assayed (i.e., does not cross react with biologically distinct structural homologs or analogs) one could then accurately measure the amount of antibody reacting with the test compound using conventional radioimmune or fluorescent competition assay techniques. This amount can then be translated into the amount of test compound present.

To date no immunochemical technique has been developed which produces a reliable, reproducibly accurate assay employing such immunochemical procedures. The problem, aside from the lack of sensitivity of available measurement techniques, has been that the antibodies produced in accordance with presently available methods are not specific for the test compound. These prior art antibodies cross-react with the biologically distinct analogs or homologs of the test compound encountered in the serum sample under assay.

Antibodies to immunogenic compounds of high molecular weight, such as proteins, can be produced by administering the unaltered or natural compound to the antibody producing host. However, small molecules which are not immunogenic by themselves, e.g. steroids, drugs of abuse, prostaglandins or catechol amines, must be bound to a high molecular weight immunogenic carrier. Furthermore, it has, in certain cases, been found desirable to couple antigenic compounds to carrier molecules, for example, in attempts to reproduce high yields of antibody to such antigens. Such artificial antigens induce antibody formation. Substances which do not induce the formation of antibody, unless bound to a high molecular weight carrier, are herein termed "haptens" in conformance with conventional usage.

Conventionally artificial antigens have been produced by conjugating immunogenic carrier molecules through the reactive functional groups on the haptenic molecule, e.g. see J. Biol. Chem., 228:713 (1957); id, 234:1090 (1958); Can. J. Biochem. Physiol., 36:1177 (1958); id., 39:941, 961 (1961); Science, 129:564 (1959); J. Immun., 92:515 (1964); Biochem. 9:331 (1970); Science, 168:1347 (1970) and J. Pharmacol. 178:253 (1971). Such attempts to produce specific antibodies by coupling carrier molecules to one of the functional groups of the hapten have successfully rendered the hapten immunogenic. However, considerable cross reactivity is demonstrated by biologically distinct structural analogs coupled at the same or similar sites. Such non-specific binding with related compounds negates the specificity of these conventionally produced prior art antibodies. See Steroids, 16:387 (1970); id 18:555, 593, 605 (1971); Karolinska Symposia on Research Methods In Reproductive Endocrinology, p. 320, Ed. E. Diczfalusky Bogtrykksiut Forum, Copenhagen (1970) and "Immunologic Methods in Steroid Determination", Eds. Peron and Caldwell, Appleton-Century-Crofts, New York (1970), p. 41.

Another approach to the preparation of specific antibodies to small molecules involved coupling the immunogenic carrier directly into the aromatic ring of the hapten. For example, see Immunochemistry 5:55 (1968) describing the synthesis of certain immunogenic steroid-protein conjugates and the production of rabbit antiserum to beta-estradiol, coupled to bovine serum ilbunin (BSA) and keyhole limpet hemocyanin (KLH). Antisera were tested against steroids coupled to human gamma globulin (IgG). The immunological assays employed quantitative precipitin and hapten inhibition tests. The conjugates produced in accordance with the method described in this paper did not produce antibodies which were specific for the steriod hapten (i.e. beta-estradiol, estriol and estrone) employed in the conjugate. Antibody to estradiol-KLH brought down a non-specific precipitate with testosterone-IgG, and antibody to estriol-KLH brought down a precipitate (nonspecifically) with testosterone-IgG and with estradiol-IgG. For a similar approach, see also Chem. Abstracts, 39:1505 (1945) in which azo proteins of morphine and strychnine were alleged to have been prepared by coupling to diazotized acetyl-p-phenylenediamine. Antibodies generated with the immunogens prepared in accordance with this paper also exhibit undesirable cross reactivity.

Most recently an attempt to produce specific antibodies for 17-beta-estradiol by coupling bovine serum albumin via the alicylic $C_6$ position was reported in Steroids, 18:605 (1971). The reported results do not support the claimed specificity.

Therefore, to the best of my knowledge, the art is devoid of a method, empolying artificial antigens for preparation of purified antibodies which are indeed truly specific; that is, antibodies which do not cross react to any significant extent with biologically distinct, structural analogs or homologs of the native homologous hapten or antigen.

To understand the importance of specificity to practical immunochemical competition assays, one need only consider that morphine specific antibodies are clearly mandatory for development of a commercially practical morphine assay. Such an assay must distinguish morphine from codeine, the commonly dispensed 3-methoxy morphine, and for that matter, from the important synthetic surrogates of morphine (e.g. methadone, meperidine and pentazocine.) The same is true, for example, in the estrogen series where cross reactivity within the class (i.e. estrone, estradiol and estriol) will defeat the usefulness of the assay.

The provision of purified antibodies exhibiting such specificity is a primary object of this invention. The antibodies produced in accordance with this invention do not cross react to any significant degree with biologically distinct structural homologs or analogs of their homologous haptens or antigens.

SUMMARY OF THE INVENTION

In accordance with this invention there is provided a method for producing purified antibodies which are specific for native homologous hapten or antigen comprising (1) administering to an animal an antibody producing dose of an artificial antigen, that is, an immunogenic carrier bound to a hapten or antigen wherein the functional groups of the hapten which determine its specificity (i.e. the antigen-determinant groups) are free and capable of asserting their native determinant characteristics, (2) generating antibody, (3) obtaining a crude mixture containing antibodies from said animal, and (4) isolating purified antibodies from said crude mixture. The artificial antigens of this invention comprise a novel embodiment thereof and are described more fully hereinafter.

The term "native hapten or antigen" connotes a hapten or antigen which is unaltered structurally, chemically, or biologically.

The term "homologous hapten or antigen" connotes that hapten or antigen capaple of bending specifically with an antibody population. For example, estriol is the homologous hapten for estriol specific antibody. Therefore, as used in this invention, "heterologous hapten or antigen" is a substance, other than a homologous hapten or antigen, usually a closely related structural analog of the homologous hapten or antigen.

The purified antibodies of this invention produced with the artificial antigens thereof exhibit heretofore unobtainable specificity, in that these antibodies do not cross react to any significant degree with heterologous hapten or antigen. This unique specificity is clearly demonstrated by results of fluorescence quenching of antibody utilizing a selected derivative of the homologous native hapten in competition with (1) native homologous hapten (or antigen) and (2) related native heterologous haptens (or antigens) as more fully described hereinafter. The native homologous hapten (or antigen) quantitatively inhibits the quenching phenomena whereas the heterologous haptens (or antigens) do not. Prior art antibodies, selected on the basis of their alleged specificity, fail to distinguish the homologous compound from its closely related analogs in increasing concentrations using standard inhibition tests.

As discussed previously, it is highly desirable to have an antibody population which can distinguish a homologous hapten or antigen from closely related molecules. Such antibodies are needed for use in immunochemical competition assays employing simple physical techniques and isotope assays to rapidly measure concentrations of small molecules in urine or serum. In addition to rendering such assays accurate and reliable, a truly specific antibody obviates the need for preliminary extraction of the sample. This has immediate applicability to radioimmune assays to significantly shorten the time presently required to carry out such assays. These antibodies are also useful in conducting immunochemical competition assays using quantitative fluorescense perturbation (i.e. inhibition of quenching enhancement and polarization).

Another assay method of this invention comprises radioimmune immuno methods to assay quantitatively for

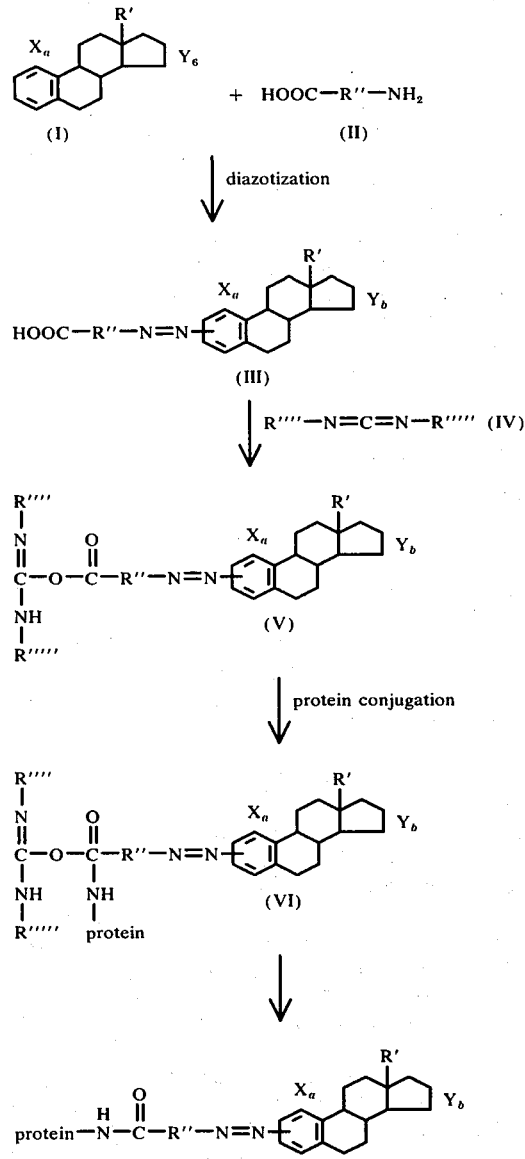

compounds of structures (I), (see attached Reaction Sequence I), herein which comprises producing a mixture, suitable for isotope counting assay of (1) a sample to be analyzed, generally from body fluid (although any sample source can be employed), (2) a known quantity of an isotopically labeled (e.g., $I^{125}$)* antibody which is specific for the compound to be assayed and (3) a hapten or antigen derivative, insolubilized by covalent linkage to a solid organic (e.g., cellulose derivative)or inorganic (e.g., amino glass) matrix (pretreated, e.g., with albumin to minimize nonspecific adsorption). The hapten or antigen derivative is homologous to said assay compound (that is, shares immunochemical specificity) so as to bind with said antibody competitively. The supernatant from this mixture is analyzed for diminution of counts per minute after incubation. This approach is unique and minimizes nonspecific adsorption as compared with present radioimmune assays.

*Other labels can be used, e.g., $I^{131}$, $C^{14}$, $I^{127}$, $S^{35}$.

Exemplary of the compounds which can be assayed are the following

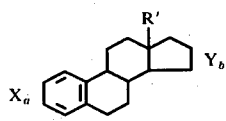

(1)

wherein X is hydrogen or a radical selected from hydroxy, keto, ester (—OR''' wherein R''' is alkyl or cycloalkyl, preferably $C_1$–$C_4$, aryl, preferably $C_6$–$C_{10}$; and includes adamantyl); primary, secondary, or tertiary amino (—$NH_2$, —NHR''', —$NR_2$'''); lower-alkyl; halo; aryl, preferably $C_6$–$C_{10}$; alkenyl; –N=NR'''; —SC ≡ N; —OOCR''; —NHCOR'''; —SR'''; —SOR'''; —NO and the like ortho or para directing groups; —$NO_2$; carboxyl; —COOR'''; —$SO_3H$; —$CF_3$; —$CCL_3$; —$NH_3$'''+; —CN; —COR'''; —$SO_3R'''$; —$IO_2$; —R'''$(OH)_2$ and the like meta directing groups; R''' is alkyl, cycloalkyl, aryl, alkenyl, cycloalkenyl, heterocyclic wherein the hetero atoms are O, S or N; Y can be the same as X and, additionally, can be any organic or inorganic substituent which is stable under the conditions utilized in the synthesis of the novel steriod-protein conjugates of this invention; R'' is hydrogen, or lower-alkyl ($C_1$–$C_4$); and $a$ and $b$ are 1 to 3.

2. psycomimetic agents as exemplified by the amphetamines, meperidine, mescaline or tetrahydrocannabinol, i.e., the active constitutent of marihuana (hashish);

3. a catecholamine, as defined before;
4. a polypeptide, as previously defined;
5. diethylstibestrol;
6. a 1⁄34,5-steriod as defined before; and
7. chlortetracycline, tetracycline and chloramphenicol.

The hapten or antigenic derivatives are covalently coupled to the solid matrix to render them insoluble. These insoluble derivatives compete with homologous underivatized hapten or antigen in the sample for antibody. The haptenic or antigenic portion of these coupled derivatives are typified by the above compounds (1–7). Illustrative of the coupled derivatives are structures I–IV (reaction sequence, above).

1. The radioimmune assay using solid phase covalently bonded hapten or antigen is as follows:

A. Establishment of Standard Curve

One ml of radioisotopic labeled* antibody (e.g., $I^{125}$) diluted 1:100–1:20,000 is added to each of a series of 20 tubes prepared for isotope counting. To each one of the tubes is also added 1 ml containing 1–10 mg of solid matrix (e.g., glass beads) covalently bound to hapten or antigen. An optimal mixture is selected (i.e., one in which 40–50% of total counts are removed from the liquid phase by insolubilized derivative. The mixture is interacted with competing underivatized hapten, i.e., assay compound, in increasing concentrations (e.g., 10–100 picograms/ml). This mixture is allowed to incubate for 8 to 12 hours at 5°–37°. After separation of clean, insolubilized material, radioactive counts of solid (or liquid) phases are measured in a scintillation counter. Control tubes contain inert IgG, uncoupled solid matrix, heterologous insolubilized hapten or antigen in the same concentrations.

*Labeling is exemplified by chloramine T method while antibody binding sites are protected on a solid immuno adsorbant. Counts per minute are $10^8$ or more in 0.20–0.50 μg/ml. Antibody is purified by chromatography.

In assaying a sample of underivatized hapten or antigen, optimally labeled (e.g., $10^8$ counts per minute in 0.20 μg/ml) antibody, purified and diluted (e.g., 1:10,000), selected for use in testing the soluble underivatized sample (hapten or antigen excess). The latter (e.g., estradiol), in increasing concentrations per ml, competes with insolubilized hapten or antigen derivative for binding with a given amount of labeled soluble antibody, will diminish the counts per minute (CPM) removed by insolubilized hapten and increase the CPM remaining in the aqueous phase (by binding with antibody). The percent of increase of CPM in the aqueous phase is directly proportional to the concentration of the underivatized hapten or antigen in test sample. The relationship is rendered linear. The more competing unaltered hapten or antigen present in the test solution, the less counts are removed by the covalently insolubilized hapten or antigen. Hence a standard curve is drawn for the test compound.

B. Assay for Underivatized Hapten or Antigen

The solution containing the sample (i.e., underivatized hapten or antigen as previously described) can be neutral aqueous solution or a body fluid (e.g., serum, urine, amniotic fluid or tissue extract).

The concentration of one unknown in the body fluid is established by counting radioactivity of the aqueous phase of the sample mixture after competition with insolubilized hapten or antigen covalently coupled to glass beads, for binding with labeled antibody. CPM are compared with the aforementioned standard curve. The control for such assay is body fluid known to contain non underivatized hapten or antigen.

Thus in carrying out the assay a sample of body fluid is obtained and is added (after solids are removed by centrifugation) in dilution to a standard mixture of antibody and insolubilized homologous hapten or antigen, the latter being present in a molar excess. The resulting solution is allowed to incubate at 5°–37° C. for 8–12 hours. Thereafter, the radioactive counts in the aqueous phase is determined, generally by a scintillation counter. The reading obtained by this instrument is compared with the standard curve for the compound under assay and translated to the concentration of sample compound present (nanograms or picograms/ml).

Another embodiment is a radioimmune assay using solid phase covalently bonded antibody wherein the isotope (label)* (e.g., $I^{125}$) is on the protein carrier moiety of the hapten-protein conjugate, rather than on the hapten moiety of prior art assays. This technique diminishes radioisotopic damage to functional groups and prevents steric hindrance.

*See footnote page 5, supra.

The soluble, labeled conjugate competes with underivatized hapten or antigen in test fluid for purified antibody (unlabeled) (or labeled with a different isotope) which is insolubilized by covalent linkage to a solid matrix (e.g., glass beads).

A. Selection of Antibody Dilution

Utilizing a standard dilution of hapten-protein conjugate (total $10^8$ CPM in 0.2 μg/ml), the insolubilized antibody is diluted 1:10–10,000 in a series of 50 tubes. A tube in which 40–60% of the total counts/min. are removed by insolubilized antibody is selected as containing the optimal ratio of antibody and marker antigen.

B. Standard Curve

The optimal mixture as selected from procedure A above is used in a series of tubes (e.g., 1–20) and into each of which is added a known amount of an underivatized hapten or antigen in nanogram or pikogram increments. After incubation for 8–12 hours at 5°–37° C., CPM are determined. The more unlabeled hapten or antigen in a given tube, the more counts are retained in the aqueous phase. The standard curve is rendered linear.

C. Assay for Underivatized Hapten or Antigen

The solution containing the sample (i.e., underivatized hapten or antigen as previously described) can be a neutral aqueous solution or body fluid (e.g., serum, urine, amniotic fluid, or tissue extract).

To establish the concentration of the unknown hapten or antigen in the body fluid, the radioactivity of the aqueous phase of the sample mixture, containing unknown hapten (or antigen), and haptenprotein conjugate (with the marker on the carrier protein) is compared, after interaction with purified antibodies covalently coupled to glass beads, with the aforementioned standard curve. The control for such assay is a liquid or body fluid known to contain no underivatized hapten or antigen.

Thus in carrying out the assay a sample of liquid or body fluid is obtained and is added (after solids are removed by centrifugation) in dilution to a standard mixture of insolubilized antibody covalently coupled to glass beads and marker proteinhapten conjugate. Hapten or antigen are in molar excess over antibody. The resulting solution is allowed to incubate at 5°–23° C. for 8–12 hours. Thereafter the radioactive counts in the aqueous phase are determined, generally by a scintillation counter. The reading from this instrument is compared with the standard curve for the compound under assay and is translated to the concentration of the compound present in nanograms or picograms per ml.

The steps of antibody production, obtaining a crude antibody mixture from the animal, and purification of antibody are fully disclosed in my copending application Ser. No. 89,929, filed Nov. 16, 1970, abandoned for example at pages 2, 24, 25 and 40.

This disclosure is incorporated herein by reference thereto.

DETAILED DESCRIPTION OF THE INVENTION

The artificial antigens of this invention can be represented by the following formula:

R—L—Z wherein R is a hapten (or antigen) group, Z is an immunogenic carrier group, and L is a linking group capable of covalently binding the carrier to the hapten. R is further characterized by the fact that all the biological determinant functional groups of the native unaltered hapten or antigen are preserved intact thereon and are therefore capable of asserting the same biologic determinant characteristics for antibody recognition as the native, unaltered molecule.

Therefore, the technique by which the immunogenic carrier is bound to R must be one which leaves all the determinant functional groups of R free to assert their biologic determinant characteristics as if no coupling reaction had occurred. (These determinant groups are well known and can be identified, for example, by inhibition of fluorescence quenching.) This is to say that the groups on R responsible for recognition by an antibody or biologic receptor are left chemically, and preferable sterically, intact and uninterfered with so that the derivatized hapten or antigen, eg. R—L—Z, is identifiable by its homologous antibody to the exclusion of closely related biologically distinct structural homologs or analogs of R. Thus the artificial antigen is recognized by the antibody population as the native unaltered molecule from which it is derived. To achieve this end all such groups must be unaltered.

The moriety R in the foregoing formula can be any group containing at least one aromatic, cyclo-olefinic, alicylic or heterocyclic moiety and bound (eg. covalently coupled) to L, preferable, at a ring atom of R. It is preferred that such moieties comprise between about 5 and about 8 ring atoms and that said ring atoms be carbon. In the case of heterocyclic moieties it is preferred that the hetero atom be nitrogen. Exemplary of such moieties are histadyl, tryptophyl, tyrosyl, phenyl, cyclopentyl, cyclohexyl, cycloheptyl cyclo-octyl, cyclopentenyl, cyclohexenyl and cycloheptenyl. It is to be understood that these cyclic moieties can be part of a fused ring system, such as napthalene, anthracene, phenanthrene and their derivatives wherein two or more ring atoms are shared by two or more rings.

The group R generally contains no more than 20 ring atoms which can be unsubstituted or substituted with one or more of such groups as hydroxy, keto, halo (eg. chloro, bromo, iodo, fluoro), carboxyl, amino, alkyl (generally containing from 1–10 carbons), alkenyl (generally 1–10 carbons and mono and polyunsaturated, generally dienyl or trienyl), phenyl and the like. Exemplary of such R groups are those derived from the native molecule by replacement of a biologically inactive substituent, i.e. a substituent, generally on a ring atom, which is not a determinant, with the substituent-L capable of coupling to an immunogenic carrier of this invention as defined more fully hereinafter.

Generally illustrative of R in its native state are any steroid (e.g. see steroids, Feiser and Fieser (1959), Reinhold Publishing Corp., New York) especially those of medical significance (eg. estradiol-17β, estrone, estriol, testosterone, cholesterol, etc.) or prostaglanding (eg. see J.E. Pike, "Prostaglandins", Scientific American, Nov. 1971, pages 84–92), narcotics (eg. alkaloids of opium such as herion, morphine, codein), barbiturates (and other CNS depressants), amphetamines (and other CNS stimulants), isomeric tetrahydrocannabinols, vitamins, (eg. see Table of Characterized Vitamins, pages 1459–60, *Blakiston's New Gould Medical Dictionary*, Second Edition (1956), McGraw-Hill, New York, N.Y.), catecholamines, eg. 1-(3,4-dihydroxyphenyl)-2-methylamino) etanol: beta-(p=hydroxyphenyl)alanine; beta-(3,4-dihydroxyphenyl)-alpha-alanine; 3,4-dihydroxyphenethylanine; 2-amino-1-(3,4-dihydroxyphenyl)ethanol; indoleamines, such as beta-3-indolylalanine; 5-hydroxytryptophan; or 5-hydroxytryptamine. Any other drugs of abuse in addition to those set forth above are important haptens of this invention. Illustrative are antihistamines, atropine, belladonna, cocaine, cyclazacine, levorphanol, LSD-25, meperidine, meprobamate, mescaline, methadone, nalophine, nitrous oxide, dimethyl tryptamine, psilocybin, scopalamine, STP (4-methyl-2,5-dimethoxy-α-methyl-phenethylamine), methedrine, demerol, the tricyclic antidepressants such as the dibenzocycloheptenes (eg. amitriptyline, nortriptyline), imipramine, the phenothiazenes, the benzoquinolizines, reserpine, the diazepoxides (eg. librium, valium), benzodiazapins. Illustrative or other hormones are diethylistilbestrol, insulin, angiotensin, thyroxin, aldosterone, growth hormone, lactogen, (bovine) insulin, follice stimulating hormone, luteinizing hormone, human chorionic gonadotropin, pitocin, adrenocorticotropin, and thyrotopin. Furthermore, R can be any polypeptide containing tryptophan, histidine or tyrosine residues (eg. see *Atlas of Protein Sequence and Structure* by M. O. Dayhoff, National Biomedical Research Foundation Silver Spring, Md., 1968, for example pages 235–272, and Vol. 4, 1969, pages D67-D172).

The immunogenic carrier group, Z in the above formula, are well known and need not be detailed. Such immunogenic substances are set forth in Cremer N. E. et al., *Methods In Immunology* (1963), W. A. Benjamine Inc., N.Y. pp. 65–113. They generally are large molecules, hence their antigenicity, having a molecular weight greater than 6000. They can be proteins, polysaccharides, polyaminoacids, polypeptides or glyco proteins containing carboxyl, hydroxyl, aryl, heterocyclic, SH, amino, or other groups suitable for selective coupling to the following coupling intermediate of this invention:

R—L wherein R is a hapten or antigen group of this invention and L is a linking group covalently bound to R and containing a reactive functional group suitable for selective coupling to a functional group of Z. Thus the main function of the linking group L is to provide a bond between the hapten (or antigen) R and the carrier Z. This bond will depend upon (1) the type of linking group L that can be introduced into R without disturbing the biological determinant characteristics of R and (2) the reactive groups on Z available for coupling. When Z is a protein, such as keyhole limpet hemocyanin (KLH, molecular weight approximately 7 million), bovine serum albumin (BSA, molecular weight 70,000) or human gamma globulin (IgG, molecular weight 150,000) the reactive functional groups on Z available for selective coupling are amino or carboxyl and RL can be tailored to couple with such groups, for example by providing an available carboxyl group for coupling to the amino function on Z or, alternatively, an available amino group to couple with the carboxyl function on Z.

The following Examples further illustrate the novel intermediates R-L.

EXAMPLE 1

A solution of 150 mg of succinic anhydride in 5 ml anhydrous pyridine is warmed and then cooled to room temperature. To this is added 314 mg. of 4-pregnen-6β-ol-3, 20-dione and the mixture allowed to stand at room temperature overnight. This mixture is then dropped slowly into a stirred mixture of 2.5 ml sulfuric acid in ice water. The precipitate is then collected and the desired product, 4-pregnen-6β-ol-3,20-dione 6-hemisuccinate, is purified by thin-layer chromatography.

EXAMPLE 2

A methanol solution containing 5% hydrochloric acid, 302 mg of 4-androsten-17β-ol-3,6-dione and 150 mg of p-carboxyphenylhydrazine is heated on a water bath at between 60°–85° C for 1–3 hours. The solution is then cooled and the precipitate filtered. The desired product, 4-androsten-17β-ol-3,6-dione 6-[p-carboxyphenylhydrazone], is purified by thin-layer chromatography.

EXAMPLE 3

A solution of 323 mg of 4-androsten-6β-chloro-17β-ol-3-one and 400 mg of mono-tetramethyl ammonium succinate in 25 ml anhydrous acetone is refluxed for 4–6 hours. The solution is then cooled and the acetone removed under reduced pressure. The residue is then chromatographed and the desired product 4-androsten-15β-ol-6hemisuccinate, purified by thin-layer chromatography.

A solution of 150 mg of succinic anhydride in 5 ml anhydrous pyridine is warmed and then cooled to room temperature. To this is added 402 mg of 5-cholesten-3β,7β-diol and the mixture allowed to stand at room temperature for 24 hrs. It is then dropped slowly into a stirred mixture of 2.5 ml of sulfuric acid in ice water. The precipitate is then collected and the desired product, 5-cholesten-3β,7β-diol-7-hemisuccinate, is purified by thin-layer chromatography.

EXAMPLE 5

A methanol solution containing 5% hydrochloric acid, 400 mg of 5-cholesten-3β-ol-7-one and 122 mg of p-carboxyphenylhydrazine is heated on a water bath at between 60°–85° C for 1–3 hours. The solution is then cooled and the precipitate filtered. The desired product, 5-cholesten-3β-ol-7-one-7-[p-carboxyphenylhydrazene], is then purrified by thin-layer chromatography.

EXAMPLE 6

A solution of 419 mg of 5-cholesten-7β-chloro-3β-ol and 400 mg of mono-tetramethylammonium succinate in 25 ml anhydrous acetone is refluxed for 4–6 hours. The solution is then cooled and the acetone removed under reduced pressure. The residue is then chromatographed and the desired product, 5-cholesten-3β-ol-7-hemisuccinate, is purified by thin-layer chromatography.

EXAMPLE 7

A solution of 150 mg of succinic anhydride in 5 ml anhydrous pyridine is warmed and then cooled to room temperature. To this is added 2.88 mg of 1,3,5(10)-estratrien-3,6α, 17-β-triol and the mixture allowed to stand at room temperature overnight. It is then dropped slowly into a stirred mixture of 2.5 ml sulfuric acid in ice water. The precipitate is then collected and the desired product, 1,3,5(10) estratrien-3,6,17β-triol-6-hemisuccinate, is purified by thin-layer chromatography.

EXAMPLE 8

A methanol solution containing 5% hydrochloric acid, 286 mg of 1,3,5(10)-estratrien-3, 17β-diol-6-one and 150 mg p-carboxyphenyl hydrazine is heated on a water bath at between 60°–85° C for 1–3 hours. The solution is then cooled and the precipitate filtered. The desired product, 1,3,5(10) estratrien-3,17β-diol-6-one-6-[p-carboxyphenyl hydrazone], is then purified by thin-layer chromatography.

EXAMPLE 9

A solution of 298 mg of 1,3,5(10)-estratrien-6β-chloro-3,15β-diol and 400 mg of mono-tetramethylammonium succinate in 25 ml anhydrous acetone is refluxed for 4–6 hours. The solution is then cooled and the acetone removed under reduced pressure. The residue is then chromatographed and the desired product, 1,3,5(10)-estratrien-3,17β-diol-6-hemisuccinate, purified by thin-layer chromatography.

EXAMPLE 10

A solution of 150 mg of succinic anhydride in 5 ml anhydrous pyridine is warmed and then cooled to room temperature. To this is added 304 mg of 6-hydroxydihydrotestosterone and the mixture allowed to stand at room temperature overnight. It is then dropped slowly into a stirred mixture of 2.5 ml sulfuric acid in ine water. The precipitate is then collected and the desired product, dihydrotestosterone-6-hemisuccinate, purified by thin-layer chromatography.

EXAMPLE 11

A methanol solution containing 5% hydrochloric acid, 304 mg of 6-keto-dihydrotestosterone and 122 mg of p-carboxyphenylhydrazine is heated on a water bath at between 60°–85° C for 1–3 hours. The solution is then cooled and the precipitate filtered. The desired product is then purified by thin-layer chromatography to yield dihydrotestosterone-6-[p-carboxyphenylhydrazone].

EXAMPLE 12

A solution of 325 mg of 6-chloro-dihydrotestosterone and 400 mg of mono-tetramethylammonium succinate in 25 ml anhydrous acetone is refluxed for 4–6 hours. The solution is then cooled and the acetone removed under reduced pressure. The residue is then chromatograped and the desired product, dihydrotestosterone-6-hemisuccinate purified by thin-layer chromatography.

EXAMPLE 13

A solution of 443 mg of 10-bromo-PGE, and 400 mg of mono-tetramethylammonium succinate in anhydrous acctone is refluxed for a period of 1–3 hours. The solution is then cooled and the acetone removed under reduced pressure. The desired product, PGE-methylester-10-hemisuccinate is then purified by standard chromatographic techniques.

EXAMPLE 14

A methanol solution containing a trace of p-toluenesulfonic acid, 314 mg of morphine-2-amino-3-methylether and 166 mg of 4-carboxybenzaldehyde is heated on a water bath at between 60°–85° C for 1–3 hours. The solution is then cooled, and the solvent removed under reduced pressure. The desired product

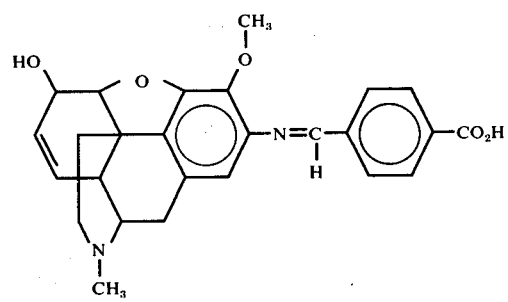

is then purified by thin-layer chromatography.

EXAMPLE 15

A solution of 314 mg 4-pregnen-6β-ol-3,20-dione and 160 mg of the 1,4 diisocyanate in anhydrous acetone is heated and then cooled to room temperature. The solvent is then removed under reduced pressure, and the product recrystallized to yield

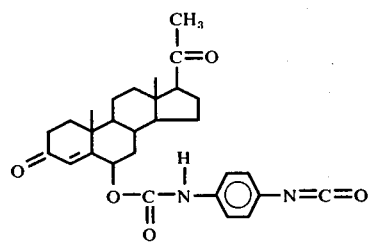

EXAMPLE 16

A solution containing 314 mg 4-pregnen-6β-ol-3,20-dione and 192 mg of the 1,4 diisothiocyanate in anhydrous acetone is warmed on a water bath and then cooled to room temperature. The solvent is then removed under reduced pressure, and the product

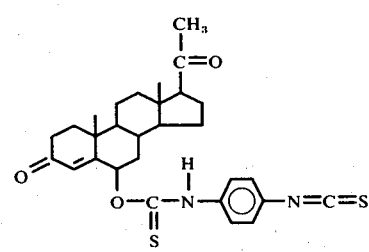

purified by recrystallization.

EXAMPLE 17

A solution containing 314 mg 4-pregnen-6β-ol-3,20-dione and 203 mg of the diacidchloride of 1,4-benzenedicarboxylic acid in anhydrous acetone is warmed on a water bath, then cooled to room temperature and the solvent removed under reduced pressure to yield

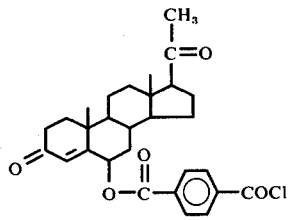

upon purification by thin-layer chromatography.

EXAMPLE 18

A methanol solution containing a trace of p-toluenesulfonic acid, 260 mg

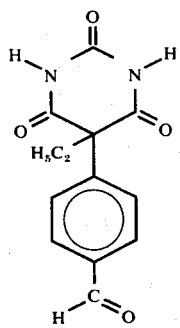

and 10 mg of p-phenylenediamine is heated on a water bath at between 70°–85° C for 1–3 hours. The solution is then cooled, and the solvent removed under reduced pressure. The desired product

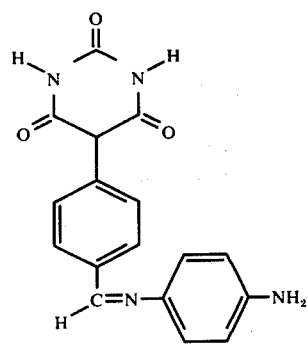

is then purified by thin-layer chromatography.

EXAMPLE 19

285 mg. of morphine is dissolved in dilute aqueous NaOH and the pH adjusted to 8. The 212 mg of the diazonium salt in cold aqueous methanol is added dropwise over a period of 1 hour to the cold alkaline morphine solution. The resulting solution is stirred for 1 hour at +5° C, then allowed to stir at room temperature for 2 hours. The pH of the solution is then adjusted to 7 and the solvent is removed under reduced pressure. The solid residue is then extracted and the product

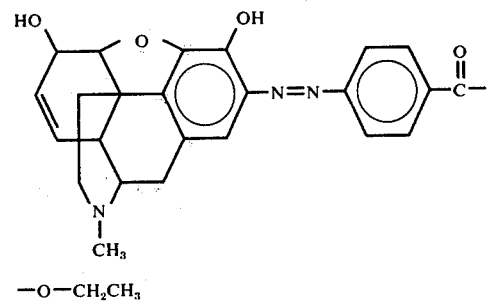

—O—CH$_2$CH$_3$ purified by column chromatography. The ethyl ester is then dissolved in 1N NaOH and allowed to remain at room temperature for 24 hours. The pH is then adjusted to 7 and the water removed under reduced pressure. The residue is then extracted and the product purified by thin-layer chromatography to yield

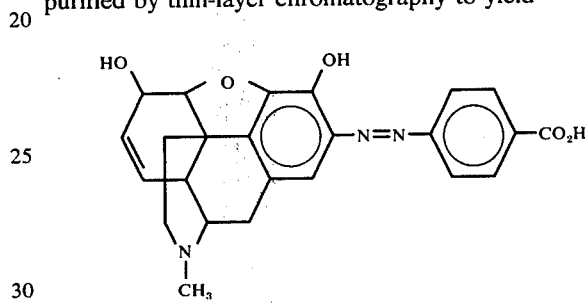

EXAMPLE 20

A methanol solution containing a trace of p-toluenesulfonic acid, 296 mg

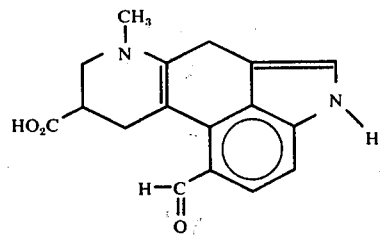

and 108 mg of p-phenylenediamine is heated on a water bath at between 70°–85° C for 1–3 hours. The solution is then cooled, and the solvent removed under reduced pressure. The desired product

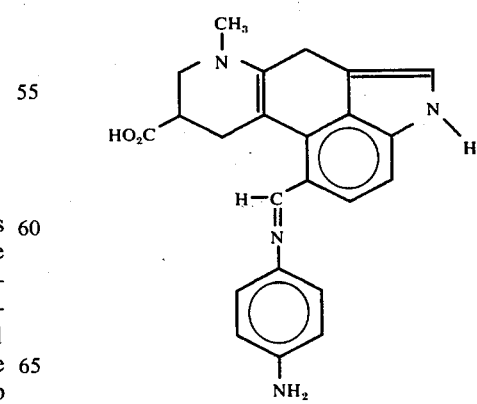

is then purified by thin-layer chromatography.

From the foregoing, it can be seen that the variety of possible linking groups L, useful in this invention, is limited only by the number of known organofunctional groups and the available sites on R for bonding. A number of different linking agents can be used in addition to those set forth in the foregoing examples. The primary criterion for such agents is that they contain two functional group - one capable of covalently bonding to R and the other capable of covalently bonding to the carrier Z. Illustrative of such functional groups are: carbonyl, carboxy, isocyano, diazo, isothiocyano, nitroso, sulfhydryl and halocarbonyl. It is not necessary to detail the possible reactions of these organic functional groups, since they are readily available from any standard organic chemistry text.

Important types of bonding between R and Z, which is provided by the linking group L, preferred in preparing the artificial antigens R-L-Z, illustrated merely by the functional or reactive groups involved, can be set forth as follows:

TYPES OF BONDING

| Bond Type | Bond Structure | Reactive Groups R—L— | Z |
|---|---|---|---|
| (1) Amide | —C—NH— | —COOH<br>—NH$_2$ | —NH$_2$<br>—COOH |
| (2) Sulfonamides | —N—C—NH— | —NH$_2$ | —NH$_2$+ClCCl |
| (3) Azo Linkage | 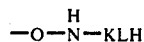 | Tyrosine<br>Histidine<br>Lysine | —N$_2$+Cl— |
| (4) Ether | RL—O—Z | —C—ONa | Z—X |
| (5) Ester | —C—O—Z | —COOH | Z——OH |
| (6) Disulfide | RL—S—S—Z | R—SH | Z--SH |

The amide bond structure is preferred for coupling protein to the novel intermediate R-L.

The novel intermediates RL of this invention can easily be coupled to the immunogenic carrier Z using conventional coupling techniques. In those cases where the functional groups available for selective coupling are —COOH on one molecule and —NH$_2$ on the other one can employ conventional carbodiimide condensation (see, for example, my copending application Ser. No. 89,929 filed Nov. 16, 1970 eg. pages 8–12 and examples 5–8.)

EXAMPLE 21

0.1 Molar 1-cyclohexyl-3-(2-morpholinoethyl)-carbodiimide metho-p-toluene sulfonate (100 mg) in a 1% saline solution is added to the purified crystalline product produced in example 19 (25 mg). The desired pseudourea intermediate is thereby produced. KLH is added to the foregoing mixture. The mixture is stirred until the intermediate azopseudourea has coupled to the KLH and is dialyzed for 2–3 days at 3° C. in 0.5M sodium carbonate, pH 8.2 until color on longer appears in dialysis solution. A final dialysis is performed against 0.9% NaCl for 24 hours. Insoluble protein is removed by centrifugation. Protein determination is made on the colored supernatant containing the following conjugate.

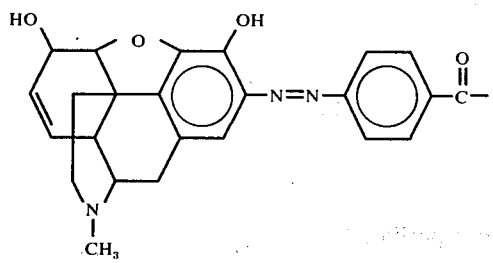

—O—N(H)—KLH

This supernatant is lyophilized after dialysis against triple distilled water.

When Example 21 is repeated with the exception that a like amount of immune gamma globulin or bovine serum albumin is substituted for KLH as the protein, the corrresponding protein conjugates are respectively produced. The reactions proceed through the corresponding intermediate proteinpseudoureas.

EXAMPLE 22

PREPARATION OF 4-(Androsten-17B-OL-3-6-dione 6-[p-carboxyphenylhydrazone]) KEYHOLE LIMPET HEMOCYANIN (KLH)

0.1 Molar 1-cyclohexyl-3-(2-morpholinoethyl) carbodiimide metho-p-toluene sulfonate (100 mg) in a 1% saline solution is added to purified crystalline 4-Androsten-17$\beta$OL-3-6-dione 6-[p-carboxyphenylhydrazone] (25 mg).

KLH is added to the foregoing mixture. The mixture is stirred until the intermediate azopseudourea had coupled to the KLH and is dialyzed for 2–3 days at 3° C in 0.5M sodium carbonate, pH 8.2 until color no longer appears in dialysis solution. A final dialysis is performed against 0.9% NaCl for 24 hours. The preceding steps remove unreacted sterioid and derivative molecules. Insoluble protein is removed by centrifugation. Protein determination is made on the colored supernatant containing the 4-Androsten-17$\beta$-OL-3-6-dione 6-[p-carboxyphenylhdrazone] KLH conjugate. This supernatant is lyophilized after dialysis against triple distilled water.

When Example 22 is repeated with the exception that a like amount of immune gamma globulin or bovine serum albumin is substituted for KLH as the protein, the 4-Androsten-17$\beta$-OL-3-6-dione 6-[p-carboxyphenylhydroazone] immune gamma globulin and the 4-Androsten-17$\beta$-OL-3-6-dione 6[p-carboxyphenylhydrazone] bovine serum albumin are respectively produced. The reactions proceed through the corresponding intermediate protein-pseudoureas.

Another method for coupling the intermediates RL to the protein involves 1) the method disclosed in Steroids 18:5, pp. 593–603, wherein an O-carboxymethyl oxime derivative (RL) is prepared and coupled to the protein through the carboxyl function of the former to primary amines of the latter.

EXAMPLE 23

A mixture of Δ 9-tetrahydrocannabinol azobenzoic acid (200 mg) and tri-butylamine (0.22 ml) is dissolved in dioxane and cooled in ice. To this mixture is added isobutylchlorocarbonate (60 μl) and the mixture left for 45 minutes keeping the temperature at 5° C. A solution of bovine serum albumin (580 mg) in a mixture of water (15.5 ml dioxane 10.3 ml) and 1N NaOH (0.58 ml) is added and the reaction mixture left for 12 hours at 5°–10° C, pH maintained at 8 with 1N NaOH.

The conjugate is dialyzed exhaustively at pH8 against 0.1M phosphate buffered saline. Conjugate is purified by centrifugation and chromatography. If purified, conjugate is to be stored, it is dialyzed against triple distilled water and lyophilized.

EXAMPLE 24

A total dose of 30–100 mg per animal of the antigen is administered (pure form) as a 1% aqueous solution (by weight of antigen) in normal saline to a New Zealand white rabbit, weighing 5 kg (males used to prepare antibodies to estrogens, otherwise sex immaterial). The antigen is administered every other day intravenously for one week (i.e., three times a week). Two weeks later an equal total dose of the antigen emulsified in an equal volume of complete Freunds adjuvant is administered subcutaneously (once only). Three weeks later blood is drawn (50 ml). Serum is separated by centrifugation. It is passed through a solid matrix, diethylaminoethylcellulose-Sephadex A50 (Pharmacia, Uppsala, Sweden) and IgG is isolated. Antibody is purified by hapten-coupled-p-aminobenzyl cellulose (e.g., estradiol-p-aminobenzyl cellulose). Specific antibody bound to the cellulose solid matrix is eluted (after repeated washing with water) by a mixture of 1 M acetic acid and 3 M freshly prepared deionized urea pH 3.2. The Table sets forth specific antibodies of this invention, and antigens used for their preparation in accordance with the foregoing procedure.

based immunoassaying, the improvement which comprises producing antibodies which are specific for native homologous hapten or antigen comprising (1) administering to an animal an antibody producing dose of an artificial antigen wherein an immunogenic carrier is bound to a hapten through a ring atom of the hapten by replacement of a biologically inactive substituent, where such substituent is not a determinant, in such manner as to leave the determinant functional groups of said hapten free, (2) obtaining a crude mixture containing antibodies from said animal, (3) isolating antibodies from said crude mixture, (4) and employing said antibodies in a radiation-based immunoassay together with a radiation label, whereby the amount of said antibodies reacting with the hapten or antigen can be measured.

2. The method of claim 1 wherein the bond between said ring atom and said immunogenic carrier is covalent, said bond being through a linking group derived from a linking agent containing one functional group capable of covalently bonding to said ring atom and another functional group capable of covalently bonding to said carrier, by coupling said functional groups to said ring atom and said immunogenic carrier.

3. The method of claim 2 wherein said hapten or antigen is selected from the group consisting of estradiol-17β, estrone, estriol, tetrahydrocannabinols, opium alkaloids, barbiturates, amphetamines, thyroxin, catechol amines, prostaglandines, vitamins, cocaine and pentazocine.

TABLE

| Antigen | Dose | Antibody Specific For |
|---|---|---|
| estradiolazobenzoyl-KLH | 30 mg | estradiol (17 β) |
| estriolazobenzoyl-KLH | 30 mg | estriol |
| estroneazobenzoyl-KLH | 20 mg | estrone |
| insulinazobenzoic | 50 mg | insulin |
| Tetrahydrocannabinol azobenzoyl-KLH 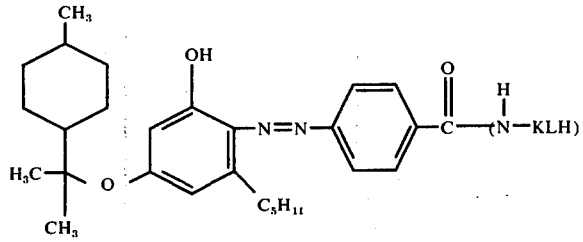 | 20 mg | tetrahydrocannabinol |
| (L-Pyroglutamyl-L-histidyl-L prolineamide) azobenzoyl-KLH 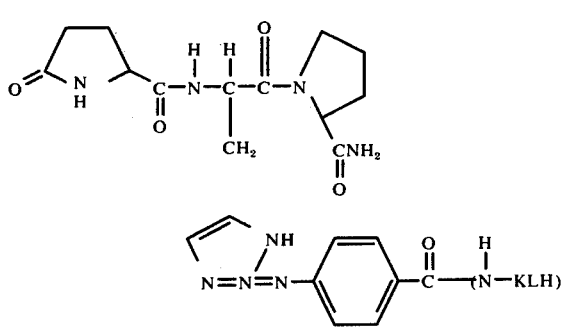 | 10 mg | thyrotropic releasing hormone |

I claim:

1. In the method of assaying for the presence and quantity of a hapten or an antigen employing radiation- 4. The method of claim 3 wherein said immunogenic carrier is an immunogenic protein.

5. The method of claim 4 wherein said protein is bovine serum albumin, keyhole limpet hemocyanin, or immunogammaglobulin.

6. The method of claim 1 wherein the hapten is selected from the group consisting of estradiol-17β, estrone, estriol, Δ-9-tetrahydrocannabinol, morphine, heroin, codeine, methadone, pentazocine, amphetamine, thyroxin, phenobarbital lysergic acid and cocaine, wherein the bond between said ring atom and said immunogenic carrier is a covalent bond via a —N=N— linkage, said linkage being a portion of a moiety capable of sustaining a diazonium ion, said moiety further including a linkage selected from the group consisting of amide, sulfonamide ether, ester or disulfide.

7. The method of claim 6 wherein said linkage between said moiety and said carrier is —CONH—.

8. the method of claim 7 wherein said immunogenic carrier is selected from the group consisting of bovine serum albumin, keyhole limpet hemocyanin, and human gamma globulin.

* * * * *